(12) United States Patent
Vachet et al.

(10) Patent No.: US 7,141,784 B2
(45) Date of Patent: Nov. 28, 2006

(54) MULTIPLEXED TANDEM MASS SPECTROMETRY

(75) Inventors: Richard W. Vachet, Belchertown, MA (US); Jonathan Wilson, Northampton, MA (US)

(73) Assignee: University of Massachusetts, Boston, MA (US)

( * ) Notice: Subject to any disclaimer, the term of this patent is extended or adjusted under 35 U.S.C. 154(b) by 0 days.

(21) Appl. No.: 11/136,127

(22) Filed: May 24, 2005

(65) Prior Publication Data

US 2005/0263693 A1  Dec. 1, 2005

Related U.S. Application Data

(60) Provisional application No. 60/573,980, filed on May 24, 2004.

(51) Int. Cl.
*H01J 49/00* (2006.01)
*B01D 59/44* (2006.01)

(52) U.S. Cl. .................. 250/282; 250/281; 250/290; 250/293

(58) Field of Classification Search ............... 250/281, 250/282, 286, 288, 290–293
See application file for complete search history.

(56) References Cited

U.S. PATENT DOCUMENTS

| | | | |
|---|---|---|---|
| 2,939,952 A | 6/1960 | Paul et al. | |
| 4,540,884 A * | 9/1985 | Stafford et al. ............ 250/282 |
| 4,736,101 A | 4/1988 | Syka et al. | |
| 4,761,675 A | 8/1988 | Sawasaki | |
| 4,931,639 A | 6/1990 | Chernyak et al. | |
| 4,978,852 A | 12/1990 | McLafferty et al. | |
| 5,143,286 A * | 9/1992 | Hansen et al. ............. 236/42 |
| 5,187,365 A * | 2/1993 | Kelley ...................... 250/282 |
| 5,196,699 A * | 3/1993 | Kelley ...................... 250/282 |
| 5,200,613 A * | 4/1993 | Kelley ...................... 250/282 |
| 5,206,507 A * | 4/1993 | Kelley ...................... 250/282 |
| 5,256,875 A * | 10/1993 | Hoekman et al. ........ 250/282 |
| 5,274,233 A * | 12/1993 | Kelley ...................... 250/282 |
| 5,381,007 A * | 1/1995 | Kelley ...................... 250/282 |
| 5,396,064 A * | 3/1995 | Wells ....................... 250/282 |
| 5,449,905 A * | 9/1995 | Hoekman et al. ........ 250/282 |
| 5,451,782 A * | 9/1995 | Kelley ...................... 250/282 |
| 5,466,931 A * | 11/1995 | Kelley ...................... 250/282 |
| 5,508,516 A * | 4/1996 | Kelley ...................... 250/282 |
| 5,517,025 A * | 5/1996 | Wells et al. .............. 250/282 |
| 5,521,380 A * | 5/1996 | Wells et al. .............. 250/282 |
| 5,608,216 A * | 3/1997 | Wells et al. .............. 250/282 |
| 5,610,397 A * | 3/1997 | Kelley ...................... 250/282 |
| 5,625,186 A * | 4/1997 | Frankevich et al. ...... 250/292 |
| 5,640,011 A * | 6/1997 | Wells ....................... 250/282 |
| 5,654,542 A | 8/1997 | Schubert et al. | |
| 5,696,376 A * | 12/1997 | Doroshenko et al. .... 250/292 |
| 5,703,358 A * | 12/1997 | Hoekman et al. ........ 250/282 |
| 6,710,336 B1 * | 3/2004 | Wells ....................... 250/292 |
| 2005/0230315 A1* | 10/2005 | Lubman et al. .......... 210/656 |
| 2005/0263693 A1* | 12/2005 | Vachet et al. ............ 250/282 |

OTHER PUBLICATIONS

Ross, C., Simonsick, W., and Aaserud, D., "Application of Stored Waveform Ion Mudulation 2D-FTICR MS/MS to the Analysis of Complex Mixtures," Anal. Chem., 74, Sep. 15, 2002, pp. 4625-4633.

(Continued)

*Primary Examiner*—Nikita Wells
*Assistant Examiner*—Bernard E. Souw
(74) *Attorney, Agent, or Firm*—Reinhart Boerner Van Deuren

(57) ABSTRACT

One or more methods for multiplexed determination and deconvolution of complex mass spectra, using quadrupole ion trap mass spectrometry.

20 Claims, 12 Drawing Sheets

OTHER PUBLICATIONS

Li., L., Masselon, C., Anderson, G., Pasa-Tolic, L, Lee, S., Shen, Y., Zhao, R. Lipton, M. Conrads. T., Tolic. N., and Smith, R., "High-Throughput Peptide Identification from Protein Digests Using Data-Dependent Multiplexed Tandem FTICR Mass Spectrometry Coupled with Capillery Liquid Chromatography." Anal. Chem. 73, Jul. 15, 2001, pp. 3312-3322.

Masselon, C., Anderson, G., Markewicz. R., Bruce, J., Pasa-Tolic, L. and Smith, R., "Accurate Mass Multiplexed Tandem Mass Spectrometry for High-Throughput Polypeptide Identification from Mixtures," Anal. Chem., 72, Apr. 15, 2000, pp. 1918-1924.

McLafferty, F., Stauffer, D., Loh, S., and Williams, E. "Hadamard Transform and 'No-Peak' Enhancement in Measurement of Tandem Fourier Transform Mass Spectra," Anal. Chem., 59, (date unknown), pp. 2212-2219.

Vachet, R., and McElvany, S., "Application of External Customized Waveforms to a Commercial Quadrupole Ion Trap," J. Am. Soo. Mass. Spectrum., Sep. 10, 1999, pp. 355-359.

Julian, R., and Cooks, R, "Broad-Band Excitation in the Quadrupole Ion Trap Mass Spectrometer Using Shaped Pulses Created with the Inverse Fourier Transform," Anal. Chem. 85, Jul. 15, 1993, pp. 1627-1633.

Williams, E. Loh, S., and McLafferty, F., "Hadamard Transform Measurement of Tandem Fourier-Transform Mass Spectra," Anal. Chem. 62, Apr. 1, 1990, pp. 698-703.

Ross, C., Guan, S., Grosshans, P., Ricca, T., Ricca, T., and Marshall, A., "Two-Dimensional Fourier Transform Ion Cyclotron Resonances Mass Spectrometry/Mass Spectrometry with Stored-Wavefrom Ion Radius Modulation," J. Am. Chem. Soc., 115, (date unknown), pp. 7854-7861.

* cited by examiner

Figure 1A
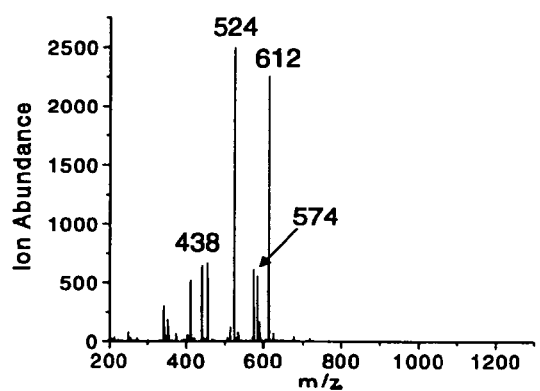
Figure 1B
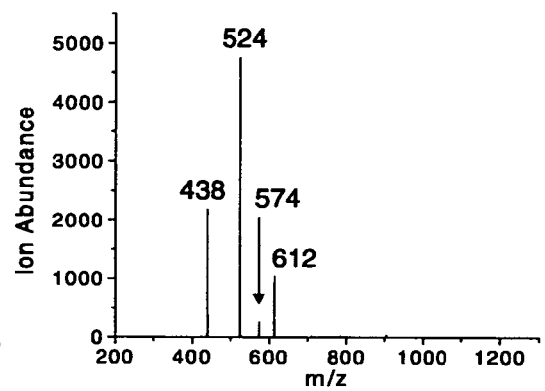
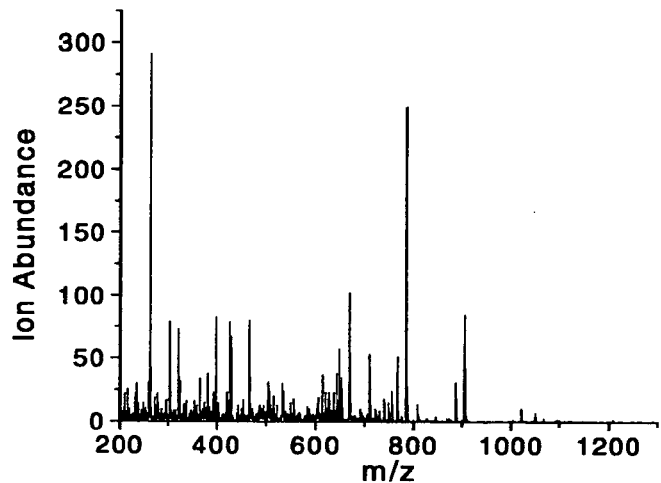
Figure 1C

MULTIPLEXED TANDEM MASS SPECTROMETRY

This application claims priority benefit of U.S. application Ser. No. 60/573,980, filed May 24, 2004, the entirety of which is incorporated herein by reference.

BACKGROUND OF THE INVENTION

Quadrupole ion trap mass spectrometers (QITMS) are used to provide rapid and sensitive analyses of a wide range of chemical and biochemical compounds. QITMSs and related spectrometric methods are known in the art and are as provided in U.S. Pat. No. 4,540,884, the entirety of which is incorporated herein by reference. Such instruments have begun to play a particularly important role in proteomics research as their favorable characteristics are applied to the identification, quantitation, and structural elucidation of peptides and proteins. One limitation with the QITMS, however, is that the structural analyses provided by this instrument is performed in a serial manner in the context of tandem mass spectrometry (MS/MS) experiments. With the emerging importance of proteomics the need for more rapid analyses are being realized.

A range of ions with different mass-to-charge (m/z) values can be trapped simultaneously in a quadrupole ion trap by the application of a radio frequency (rf) voltage to the ring electrode of the device. The trapped ions all oscillate at frequencies that are dependent on their m/z, and these frequencies can be readily calculated. MS/MS is then performed by carrying out three steps. First, the analyte ions having the single m/z of interest (parent ions) are isolated by changing the rf voltage applied to the ring electrode and by applying waveforms (i.e. appropriate ac voltages to the endcap electrodes) with the appropriate frequencies that resonantly eject all the ions but the m/z of interest. Second, the isolated parent ions are then resonantly excited via the application of another waveform that corresponds to the oscillation frequency of the parent ions. In this way, the parent ions' kinetic energies are increased, and they undergo energetic collisions with the background gas (helium), which ultimately result in their dissociation into product ions. Third, these product ions are then detected with the usual mass analysis techniques in QITMS. It is the mass differences between these product ions and their incipient parent ions that provides the structural information during this MS/MS experiment. This method of performing MS/MS is the current state-of-the art in commercial QITMS, and referred to as serial MS/MS.

Multiplexed MS/MS refers to performing MS/MS on ions of multiple m/z ratios simultaneously. A primary concern, however, is that upon isolation and dissociation of several compounds simultaneously, the product ions that are formed need to be associated with the correct parent ions in order for structural information to be gathered for each parent ion. During serial MS/MS this is accomplished by isolating and dissociating only one parent ion at a time so that the resulting products necessarily come from that parent ion. When one isolates and dissociates multiple parent ions all at once, the normal manner of relating which product ions dissociate from each parent ion is lost.

Several protocols for multiplexed MS/MS on Fourier Transform Ion Cyclotron Resonance (FTICR) mass spectrometers have been reported. Comprehensive 2-dimensional (2-D) methods analogous to 2-D NMR were used to simultaneously dissociate a collection of parent ions. Attributing the resulting product ions to the appropriate parent ions relies on a sinusoidal pattern of excitation waveforms that produces a modulation in the product ion abundances that can be later deconvoluted. Hadamard transform methods have also been used, but like the comprehensive 2-D approach multiple spectra are acquired in which different subsets of parent ions are simultaneously dissociated. The drawback to both the Hadamard method and the comprehensive 2-D approach is that these methods provide little to no timesavings as compared to the analogous serial approaches. Further, parent ion dissociations and product ion abundances do not always vary in the expected manner. Encoding is dependent upon known changes in parent ion kinetic energy, but product ion abundances do not necessarily change in a direct manner as parent ion kinetic energies (and, thus, collision energies) are changed. The net result is that product ions may be associated with incorrect parent ions.

Another approach developed recently allows product ion spectra to be obtained from multiple parent ions in a single mass spectrum, which significantly enhances the throughput. Because MS/MS analyses on FTICR mass spectrometers are inherently slower than MS/MS analyses on QITMS, this method is noticeably slower. Furthermore, this approach relies on the high mass accuracy of the FTICR to identify product ions from different parent ions by exact mass and database searching. Consequently, this method necessitates the high performance capabilities offered only by FTICR spectrometers, and therefore is not suitable for cheaper and more widely accessible mass spectrometers like QITMS. Further, this method depends upon the compound of interest present in an accessible data base and effective search capabilities—without which the analysis is unworkable.

BRIEF DESCRIPTION OF THE DRAWINGS

FIG. 1: (A) Mass spectrum of a collection of peptide ions. (B) Spectrum obtained after simultaneously isolating 4 parent ions. (C) Spectrum obtained after simultaneously dissociating the 4 parent ions

SUMMARY OF THE INVENTION

Figure 2A:
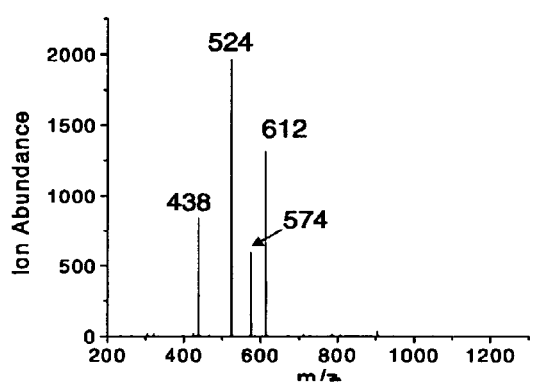
FIG. 2: (A) Spectrum obtained after simultaneously isolating 4 parent ions under different accumulation conditions. (B) Spectrum obtained after simultaneously dissociating 4 parent ions in A.

In light of the foregoing, it is an object of the present invention to provide one or more multiplexed tandem mass spectrometric methods, thereby overcoming various deficiencies and shortcomings of the prior art, including those outlined above. It will be understood by those skilled in the art that one or more aspects of this invention can meet certain objectives, while one or more other aspects can meet certain other objectives. Each objective may not apply equally, in all its respects, to every aspect of this invention. As such, the following objects can be viewed in the alternative with respect to any one aspect of this invention.

It is an object of the present invention to provide a methodology for encoding, simultaneously, product ions originating from multiple parent ions.

It is another object of the present invention to provide one or more multiplexed tandem mass spectrometric methods more efficiently from both a cost and time perspective, as compared to analogous serial methods of the prior art.

It is another object of the present invention to provide a method for direct encoding of multiple parent ion abundances, thereby avoiding the inherent non-linearity between collision energies and product ion abundances of the sort which accompany the two-dimensional methods of the prior art.

It is a further object of the present invention to provide multiplexed or multiplexed mass spectrometric methods without reliance on data base comparison or search capabilities.

Other objects, features, benefits and advantages of the present invention will be apparent from this summary and its descriptions of various embodiments, and will be readily apparent to those skilled in the art having knowledge of mass spectrometric methods and analyses. Such objects, features, benefits and advantages will be apparent from the above as taken in conjunction with the accompanied examples, data, figures and all reasonable inferences to be drawn therefrom, alone or with consideration of the references incorporated herein.

Accordingly, the present invention can be directed to a method for multiplexed tandem mass spectrometry. Such a method comprises (1) providing first spectra comprising a spectrum of a plurality of compound parent ions, and a spectrum of at least one product ion of each parent ion, the first spectra acquired under a first set of ion trapping conditions; (2) providing secondspectra comprising a spectrum of a plurality of compound parent ions, and a spectrum of at least one product ion of each parent ion, the second spectra acquired under a second set of ion trapping conditions; (3) determining the fractional change in each parent ion accumulated over the first and second spectra; and (4) applying the fractional change to at least one of the product ions in the first and second product ion spectra, to determine product ions for each parent ion.

Trapping conditions can be selected from conditions which would be known to those skilled in the art made aware of this invention, and can include conditions selected from at least one of rf voltage applied to a ring electrode during accumulation, and a predetermined low m/z cut off. The spectra can be acquired over different applied rf voltages, or such cut off values, as expressed by relationships defined more fully, below. Depending upon factors including the number of compounds to be resolved or the degree of resolution required, such a method can further comprise providing third spectra comprising a spectrum of a plurality of compound parent ions, and a spectrum of at least one product ion for each parent ion, the third spectra acquired under a third set of trapping conditions. Regardless, such a method can further comprise use of a liquid chromatographic separation either for before or after product ion determination.

From an alternative perspective, the present invention can also be directed to a method of using quadrupole ion trapping mass spectrometry for multiplexed determination of multiple parent/product ion relationships. Such a method comprises (1) providing a quadrupole ion mass spectrometer; (2) providing at least two mass spectra, each spectrum comprising product ions of a plurality of parent ions, with each spectrum generated at a different rf voltage (or, at a different low m/z cut off value); (2) calculating a fractional change in ion abundance (or, ion intensity) for each parent ion upon change in product ion accumulation; and (3) determining product ions having a change in abundance, from one spectrum to another, according to the calculated fractional change for each parent ion.

The parent ion spectrum can be derived from multiple, two or more analytes or compounds of interest, simultaneously, as may be provided by way of a compound mixture.

Embodiments of this inventive methodology can be used in conjunction for the structural analysis of multiple or a mixture of peptide compounds; however, without limitation, a range of non-peptide analytes are also contemplated as would be understood by those skilled in the art made aware of this invention. While certain embodiments are described in conjunction with first and second product ion spectra, one or more additional spectra can be utilized as described herein, depending upon the number of compounds in a mixture, parent ions analyzed and/or accuracy desired. The mass spectrometric methods of this invention can be used alone or in conjunction with one or more structural or separatory techniques, including but not limited to high pressure liquid chromatography.

In part, the present invention can also comprise a method of using Gaussian distribution to assess a product ion mass spectrum. Such a method comprises (1) providing an m/z parent ion accumulation exhibiting a Gaussian distribution as a function of ion detection conditions, the parent ion having a detection condition (optimal in certain embodiments), with the distribution providing a center value, c, and a width value, w, for each accumulation; (2) determining a fractional change in parent ion accumulation according to the relationship(s) described, herein; and (3) applying the fractional change to a first product ion spectrum to assess a second product ion spectrum, to associate product ion spectra with a corresponding parent ion. While detection and/or trapping conditions associated with this invention can be described in terms of rf voltages, it is understood in the art, as illustrated in several examples, that corresponding values for low m/z cutoffs (LMCO) can be used as provided directly via the spectrometric instrumentation used. Likewise, equation 1 or a variation of the relationship provided therein, using LMCO values in the manner shown, can be used with comparable effect.

DETAILED DESCRIPTION OF CERTAIN EMBODIMENTS

More particularly, to illustrate several non-limiting embodiments, after an initial or first product ion spectrum (i.e., primary spectrum) is taken for each of the parent ions simultaneously, another or second product ion spectrum (i.e., secondary spectrum) is acquired with the abundances corresponding to each parent ion changed by a known amount. By doing this the product ions are encoded for by the abundance change of their parent ion. For example, in FIG. 1, four parent ions from the initial mass spectrum (FIG. 1A) are isolated (FIG. 1B) and simultaneously dissociated to give a primary product ion spectrum (FIG. 1C). Then the same parent ions (FIG. 1B) are simultaneously dissociated to obtain a secondary product ion spectrum (FIG. 2B) after changing their abundances. The product ions of each parent ion can then be determined by observing their resulting abundance change, which should be correlated with the abundance change of their associated parent ion.

FIG. 2A shows the associated abundance change of each parent ion. An initial assumption is that the likelihood that two different parent ions will dissociate to the same product ion m/z is very low. This assumption allows one to overcome an obvious conundrum, which can be expressed most clearly by drawing an analogy to mathematically solving for a set of unknowns. Usually to solve for n unknowns one needs n equations. However, with this methodology, product ion spectra are solved for 4 parent ions, using only 2 spectral acquisitions in conjunction with a constraint on the possible values for the unknowns. (Note: the spectra shown in FIGS. 1B and 2A are hypothetical and for illustration purposes only.)

The approach described above is not limited to 2–4 parent ions but is applicable, without limitation, to mass spectra of more complex systems. A timesaving feature of this approach is that structural information can be gathered from multiple, n, parent ions in as few as 2 product ion spectra. Of course, as the number of parent ions increases the likelihood that more than one parent ion will dissociate to product ions of the same m/z will increase. To address this potentiality, a third product ion spectrum (or tertiary spectrum) can be acquired in which the parent ion abundances are changed to another fraction/multiple of their initial abundances. Then, for any given product ion, simple matrix algebra could be used to deconvolute the data.

Figure 3A:
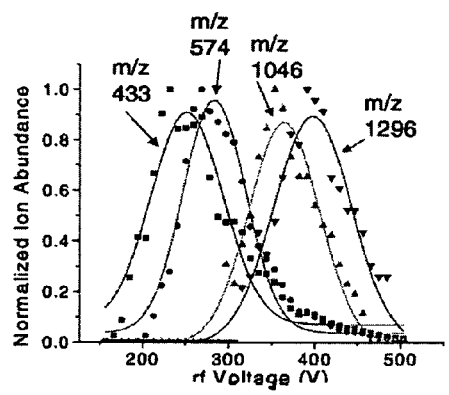
FIG. 3: (A) Normalized ion abundances as a function of the rf voltage during ion accumulation. (B) rf voltage required for optimum ion accumulation as a function of ion m/z ratio.
Figure 3B:
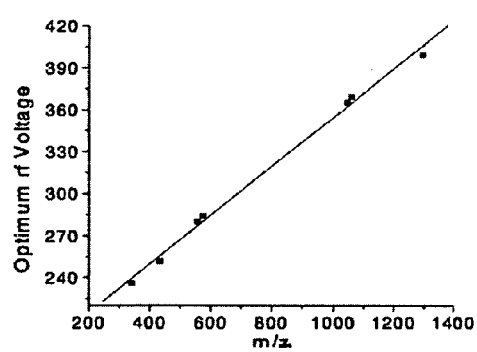

Changing the parent ion abundances in a known way from one product ion spectrum to the next provides and enables the intensity encoding scheme for the multiplexed MS/MS of this invention. Change in the parent ion abundance can be accomplished by accumulating the parent ions in the primary spectrum and the secondary spectrum under different trapping conditions. The rf voltage applied to the ring electrode during ion accumulation can be changed from one value to another in going from the primary spectrum to the secondary spectrum. The resulting changes in parent ion abundances reflect a feature of ion accumulation in the QITMS: the efficiency of ion accumulation changes in a mass-dependent fashion as the rf voltage is changed. This phenomenon is illustrated in FIG. 3. As the rf voltage is increased, ions of higher m/z are more efficiently accumulated. From FIG. 3 it is important to note two things. First, the change in ion abundance as a function of rf voltage exhibits a Gaussian distribution (FIG. 3A). Second, for different m/z ions there exists an optimum rf voltage at which the ions are most efficiently accumulated. The optimum rf voltage clearly increases as the m/z of the ion increases (FIG. 3B).

Because Gaussian distributions are well-understood mathematical functions, the abundance changes of any m/z ratios of interest can be predicted upon changing the rf accumulation voltage as long as the center and the width (at ½ height) of the Gaussians are known. For the peptide ions, for example, the relationship between the center of the Gaussian distribution and m/z is linear (FIG. 3B), which has been observed previously in the art. Furthermore, the widths (at ½ height) of the Gaussian peaks seem to be relatively constant at a value of 41±3 V. Such a value may vary from instrument to instrument and may be somewhat dependent upon operating conditions. Accordingly, an instrument or apparatus used in conjunction with one of the present methods may be calibrated. Nonetheless, typical values can be of the sort described herein.

Figure 2B:
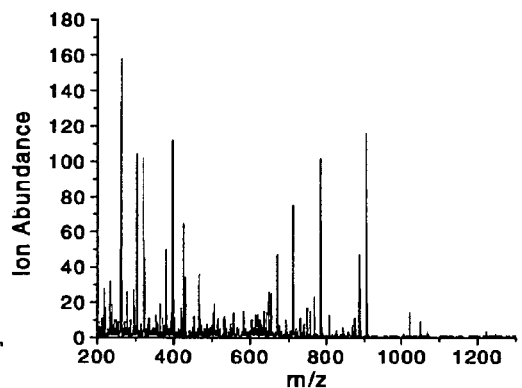

Referring back to the data in FIGS. 1C and 2B, the parent ion abundance changes and thus the product ion abundance changes, which allow the appropriate parent/product ion relationships to be established, can be predicted by determining the Gaussian distributions for each ion. The Gaussian center and width are used to determine this distribution, and a normalization factor is used to ensure a valid comparison of ion abundances between the primary and secondary spectra. The corresponding center for a particular m/z parent ion can be determined using a relationship illustrated in FIG. 3B, the width is 41 V, and a normalization factor can be applied. The fractional change in abundance ($F_{1-2}$) in going from the primary (i.e., first product ion) spectrum (FIG. 1C) to the secondary (i.e., second product ion) spectrum (FIG. 2B) can then be determined by applying the Gaussian center and width to equation 1, where rf1 and rf2 are the rf accumulation voltages used for the primary and secondary spectra, c is the center of the Gaussian, and w is the Gaussian width. Using equation 1 the expected fractional $$F_{1-2} = \frac{e^{\left(\frac{-(rf2-c)^2}{2w^2}\right)}}{e^{\left(\frac{-(rf1-c)^2}{2w^2}\right)}} \quad (1)$$

change in ion abundance for the parent ion at m/z 524, for example, is 0.41. The product ions whose abundances change by approximately this amount in the secondary spectrum (FIG. 2B) are the ions at m/z 784 (0.40), 669 (0.46), 647 (0.45), 466 (0.38), and 263 (0.50). Such ion abundance changes allow these product ions to be associated with the parent ion at m/z 524. This process can be repeated for each of the parent ions in order to determine all the appropriate parent/product ion relationships. In this way the multiplexed MS/MS data can be deconvoluted to determine the individual product ion spectra for each of the five parent ions used in this illustration.

The product ion spectra for 4 parent ions can be acquired in 50% of the time it would have taken to acquire the individual product ion spectra using serial MS/MS (i.e., 2 vs. 4 spectra), a significant increase in efficiency. An associated increase in throughput allows, for instance, structural interrogation of 4 parent ions co-eluting from a high-performance liquid chromatographic (HPLC) run. Whereas by serial MS/MS, structural information for only 2 of these parent ions might be attainable. Multiplexed MS/MS on a greater number of parent ions leads to an even greater relative reduction in analysis time.

Further, this invention represents an improvement over existing QITMS technology by way of possible structural analyses of complex compound mixtures. Often liquid chromatography (LC) is combined with MS to facilitate the study of mixtures. LC is used to separate a mixture into its components, and then the separated components are introduced into the mass spectrometer one at a time for structural analysis. In cases where short analysis times are necessary, LC runs are often substantially shortened. As a consequence more components elute into the mass spectrometer simultaneously. If, for example, multiple compounds elute into the mass spectrometer during a 4 sec period, serial MS/MS on the QITMS would likely only allow two parent ions to be structurally analyzed. In contrast, the present multiplexed MS/MS technique allows all of the co-eluting parent ions to be structurally analyzed, which would maximize the available information.

EXAMPLES OF THE INVENTION

The following non-limiting examples and data illustrate various aspects and features relating to the methods of the present invention. In comparison with the prior art, the present methods provide results and data which are surprising, unexpected and contrary thereto. While the utility of this invention is illustrated through the use of several peptide or protein mixtures, it will be understood by those skilled in the art that comparable results are obtainable with various other compounds or number thereof, as commensurate with the scope of this invention.

Likewise, the methods of this invention can be practiced without limitation as to any one QITMS apparatus, component configuration or associated software. For instance, while isolated parent ions can be described as resonantly excited via waveforms corresponding to their oscillation frequencies to induce energetic collisions with a background gas (e.g., helium) and dissociation into product ions, those skilled in the art would understand other methods to achieve dissociation into product ions in a quadrupole ion trap. For instance, with appropriate component modification, photons from infrared lasers can be used to dissociate parent ions. Various other QITMS apparatus and component configurations, together with related software, programs and associated hardware, are commercially-available and known in the art. For example, reference is made to the aforementioned, incorporated '884 patent, in particular FIGS. 1–2 thereof, such apparatus and components as can be used herewith, through straight-forward modifications thereof, as would be understood by those skilled in the art made aware of this invention.

Example 1

Figure 4:
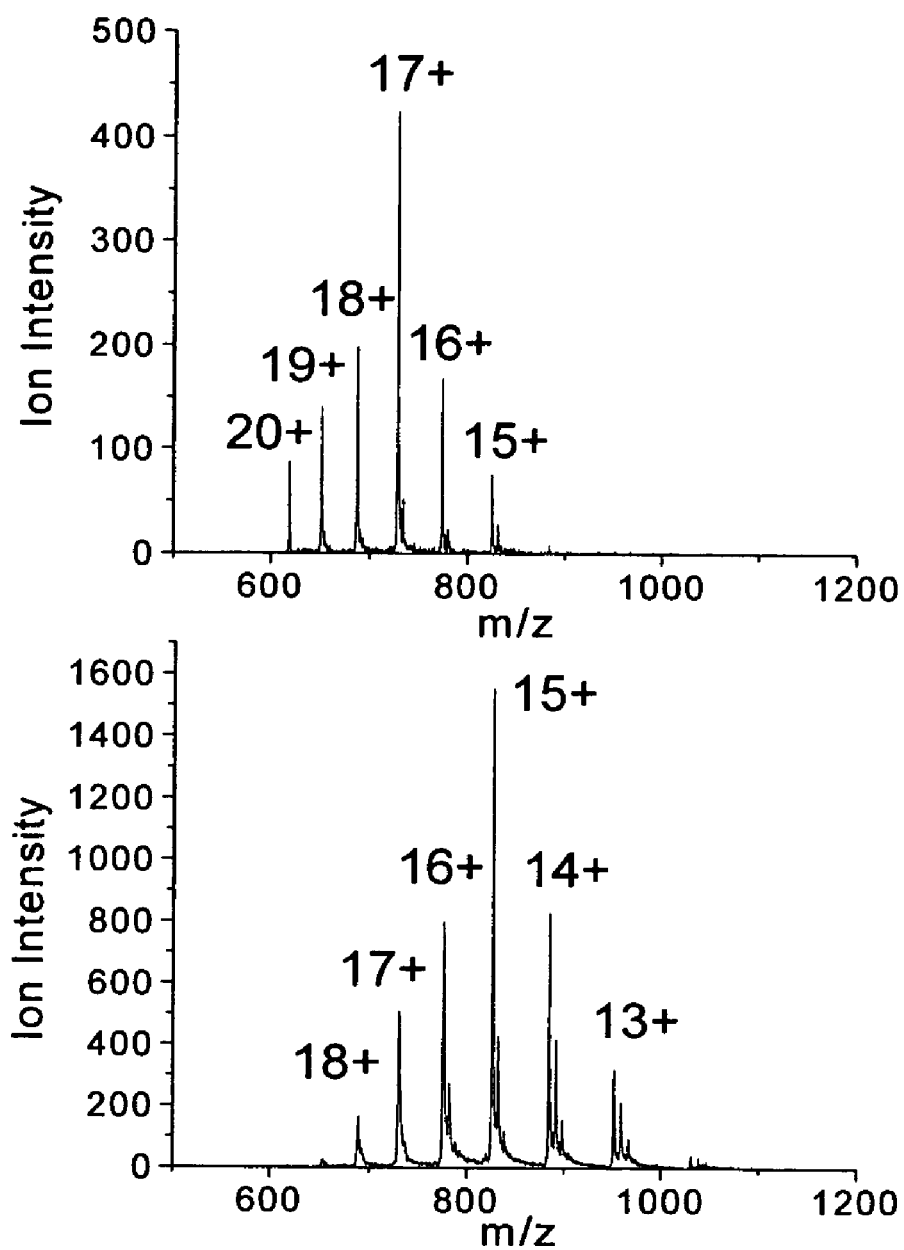
FIG. 4: Mass spectra of cytochrome c at LMCO values of (A) 41 and (B) 51.
Figure 5:
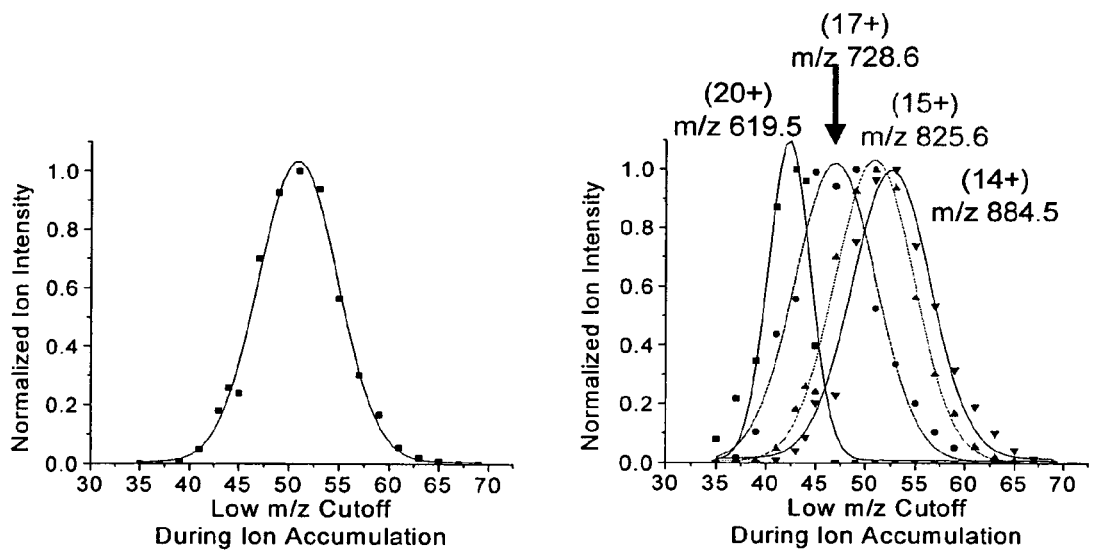
FIG. 5: (A) Normalized ion intensity distribution for the +15 charge state of cytochrome c as a function of LMCO during ion accumulation. (B) Normalized ion intensity distribution for the +14, +15, +17, and +20 charge states of cytochrome c as a function of LMCO during ion accumulation.

As discussed above, a commonly considered disadvantage of quadrupole ion trap mass spectrometers is the limited and variable m/z range over which ions can be efficiently accumulated from external ion sources. This fact is illustrated in FIG. 4, which shows the mass spectra of the protein cytochrome c at two different rf accumulation voltages. In FIG. 4A cytochrome c charge states ranging from +15 to +20 are apparent when the rf voltage applied to the ring electrode during ion accumulation is such that the low m/z cutoff (LMCO) is 41 Da, which corresponds to an rf voltage of approximately 257 $V_{p-p}$. When the rf accumulation voltage is increased to 320 $V_{p-p}$ (LMCO=51 Da) during ion accumulation, the cytochrome c mass spectrum (FIG. 4B) clearly changes so that charge states between +13 and +18 are apparent. If the normalized ion intensity of the +15 charge state is plotted over a range of LMCO values, it is clear that a Gaussian distribution represents the relationship between ion intensity and LMCO during ion accumulation (FIG. 5A). Furthermore, plotting the normalized ion intensities of other charge states results in Gaussian distributions that differ by center of the distribution, and the distribution center increases as the mass-to-charge ratio (m/z) of the ion increases.

Example 2

Figure 6:
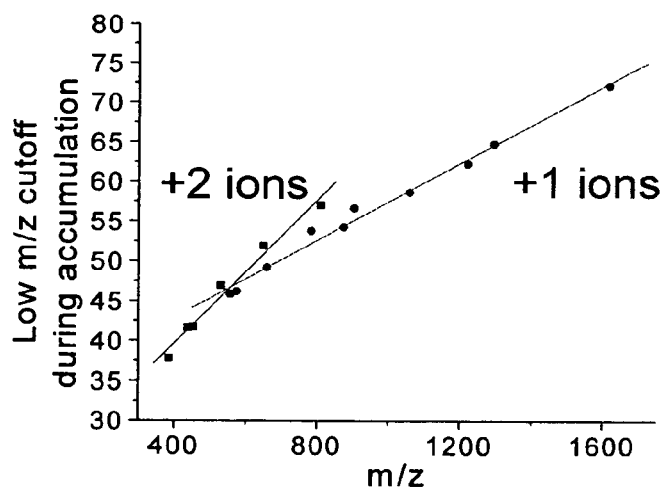
FIG. 6: Plot of the optimum LMCO during ion accumulation as a function of peptide ion m/z.
Figure 7:
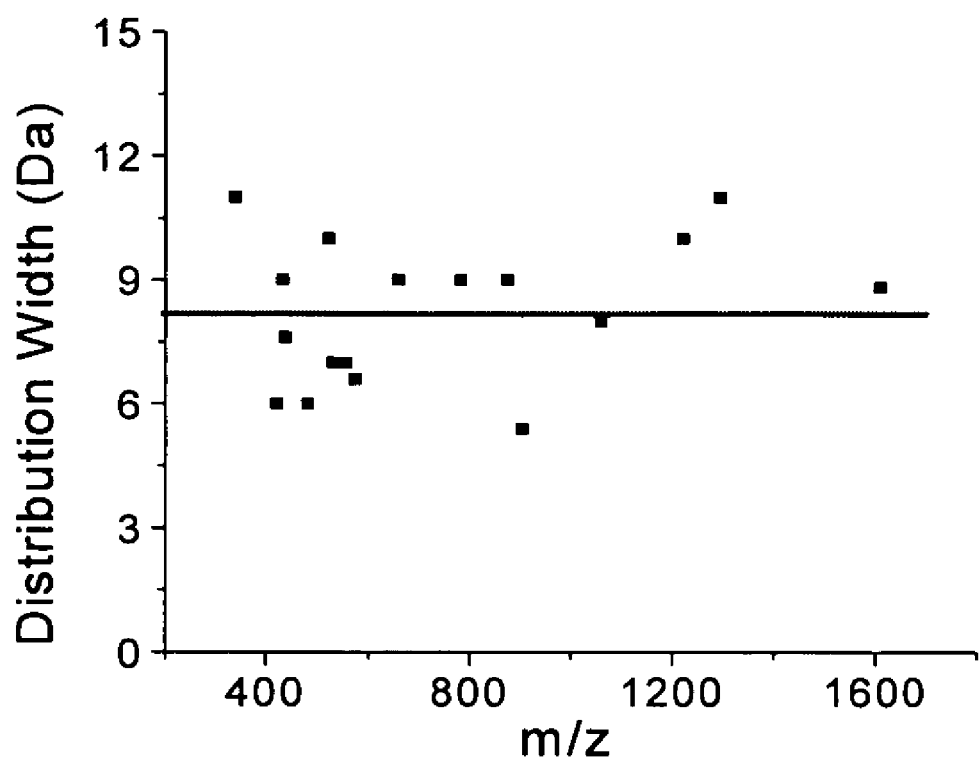
FIG. 7: Plot of the width of the Gaussian distribution (in LMCO units [Da]) as a function of peptide ion m/z. The average width of 8 Da is shown by the line through the data.

A series of 16 peptide ions were studied to observe the relationship between ion intensity and the LMCO during ion accumulation. Just as in the preceding example, the distribution of ion intensity as a function of LMCO is also Gaussian in nature. Moreover, there is a linear relationship between the optimum LMCO during accumulation and peptide ion m/z, as illustrated in FIG. 6. The slope of this linear relationship differs for peptide ions with a +1 charge state as compared to peptide ions with a +2 charge state. For the +1 peptide ions, the equation for the line in FIG. 3 is y=0.024x+33.2, while for the +2 peptide ions the equation is y=0.045x+21.7. The width (at 50%) of the Gaussian distribution does not have any apparent relationship with peptide ion m/z as evidenced by FIG. 7. Within experimental error, the Gaussian widths (at 50%) appear to be about 8 Da. Both the Gaussian centers and widths are somewhat dependent upon the parameters used to transport the ions from the electrospray ion source to the quadrupole ion trap. These parameters were held constant during all the studies described, below. Optimal application of this intensity encoding scheme can depend upon instrumental calibration to determine the appropriate Gaussian widths and the equations that relate the Gaussian centers to m/z values.

Figure 8:
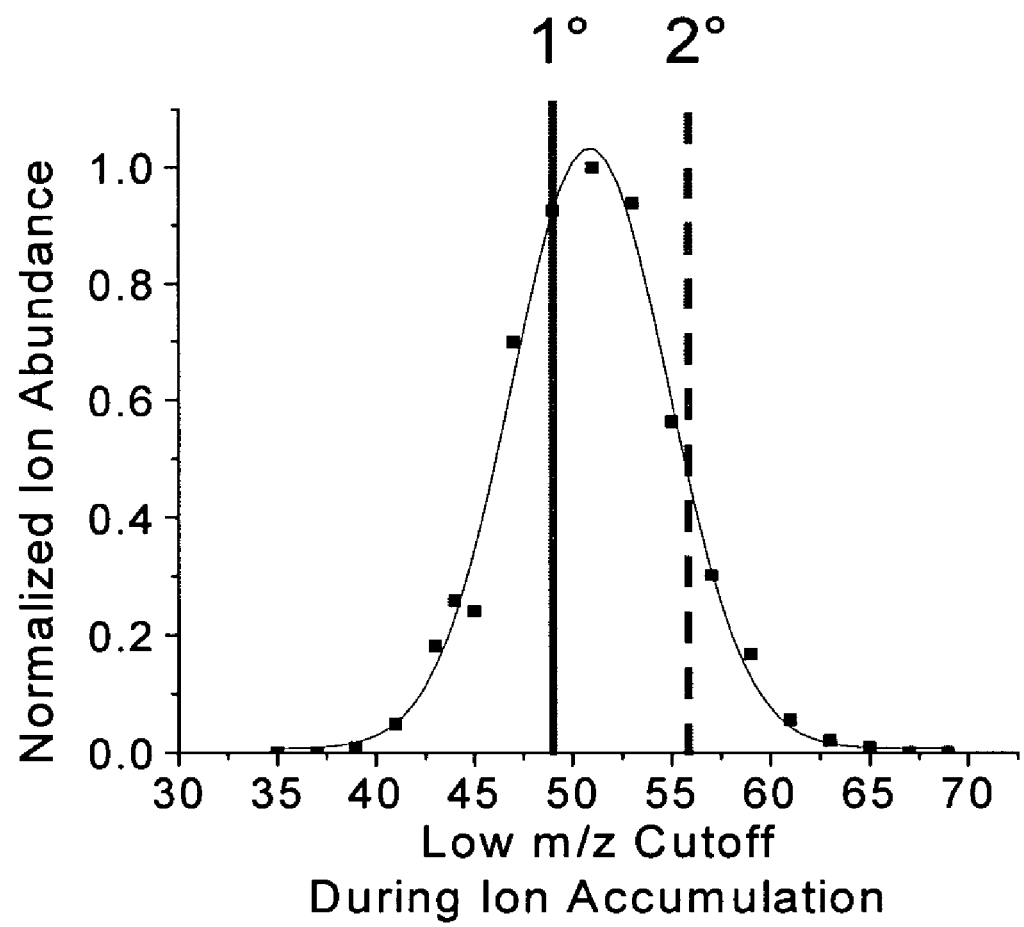
FIG. 8: Illustration of how intensity encoding is accomplished. Acquisition of the primary spectrum (1°) is carried out at the LMCO value shown by the solid line, and acquisition of the secondary spectrum (2°) is carried out at the LMCO value shown by the dotted line. The ion intensity change is then predicted using equation 1.

As demonstrated above, the reproducible Gaussian relationship between ion intensity and LMCO during ion accumulation allows the development of an intensity encoding scheme for multiplexed MS/MS. Application of this intensity encoding scheme is illustrated in FIG. 8. If a given set of parent ions is accumulated at one LMCO (or rf voltage, V) during the acquisition of the primary spectrum and then at a different LMCO (or rf voltage, V) during the acquisition of the secondary spectrum, the ions' changes in intensities can be predicted based upon the known Gaussian distributions. Equation 1 is used to calculate this fractional intensity change. In a variation of the relationship given by equation 1 LMCO (1°) (i.e., corresponding to rf1) is the low m/z cutoff used for ion accumulation in a first or primary spectrum, LMCO (2°) (i.e., corresponding to rf2) is the low m/z cutoff used for ion accumulation in a second or secondary spectrum, c is the center of the Gaussian distribution, which is m/z dependent and can be determined from lines in FIG. 6, and w is the width (at 50%) of the Gaussian distribution, which is equal to ~8 Da for each parent ion.

$$F_{1°-2°} = \frac{e^{\left(\frac{-[LMCO(1°)-c]^2}{2w^2}\right)}}{e^{\left(\frac{-[LMCO(2°)-c]^2}{2w^2}\right)}} \quad (2)$$

Example 3

The data of Examples 3a–3e were acquired using a Bruker Esquire-LC quadrupole ion trap mass spectrometer. The following Esquire parameters were used for generation of the spectra. All parameters are subject to change depending on the compounds analyzed and corresponding experimental procedure. Some parameters vary slightly from day-to-day and are chosen to optimize a particular instrument response. These parameters are noted with and asterisk (*). The parameters noted with a plus sign (+) are optimally kept as constant as possible, as they appear to affect Gaussian width and center values, more so than others.

| | |
|---|---|
| *Capillary | −3000 V |
| *End Plate Offset | −500 V |
| *Nebulizer | 5 psi |
| *Dry gas | 3 L/min |
| *Dry temp. | 300 C |
| +Skimmer 1 | 30 V |
| +Skimmer 2 | 10 V |
| +Capillary Exit Offset | 80 V |
| +Capillary Exit | 110 V |
| +Octopole | 2.70 V |
| +Octopole Delta | 2.50 V |
| *Octopole RF | 175 V(p—p) |
| *Lens 1 | −5 V |
| *Lens 2 | −60 V |
| Mulitplier | −1370 V |
| Dynode | −7 kV |
| Scan Delay | 0.50 ms |
| Scan | 50 to 1650* |
| Isolation Delay | 0 ms |
| Fragmentation Delay | 10 ms |
| Esquire Isolation mass | 318 − approx qz 0.8 |
| +SWIFT dissociation time | 65 ms |
| +SWIFT isolation time | 65 ms |
| +SWIFT dissociation amplitude | 2 V(p—p) for all ions |
| +SWIFT isolation voltage | 10 V(p—p) for all ions |
| +SWIFT dissociation width | 10 m/z units centered around ion of interest |
| +SWIFT isolation width | 10 m/z units centered around ion of interest |

SWIFT is an algorithm used to help isolate and dissociate parent ions. The SWIFT waveforms were calculated using a program written in LabView 6.0 and then downloaded to a Wavetek, Model 39 arbitrary waveform generator. A Stanford Research Systems, INC., Model DG535 digital pulse generator was then used to apply the SWIFT isolation and dissociation waveforms with the appropriate timing to the entrance endcap electrode of the Bruker Esquire-LC. Nonetheless, in conjunction with this invention, various other methods can be used to facilitate ion isolation and dissociation. Likewise, as would be understood by those skilled in the art, other hardware components can be used to generate appropriate waveforms.

The collected mass spectral data was exported from Bruker's Data Analysis program into Microcal Origin 6.0 for further data processing. Origin 6.0 was also used to fit the Gaussian peaks and calculate the fractional changes from one point on the Gaussian distribution to another.

Example 3a

Figure 9:
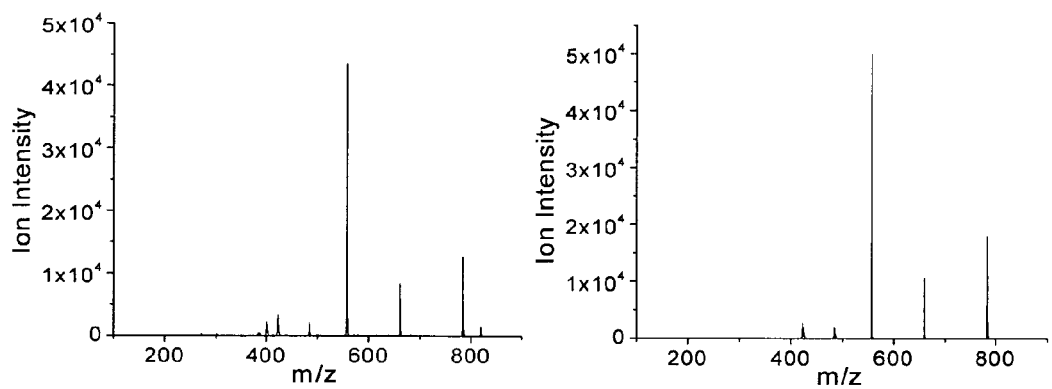
FIG. 9: (A) Mass spectrum of a mixture of 5 peptides (TRH-Gly, angiotensinogen, leucine enkephalin, β-casomorphin, and leucokinin) acquired at a LMCO value of 48 Da. (B) Mass spectrum of same mixture of peptide ions after SWIFT isolation at a LMCO value of 48 Da.

The intensity encoding aspect of this invention was applied to a collection of 5 peptide ions, as illustrated in the following. A mixture of 5 peptide, including TRH-Gly, angiotensinogen, leucine enkephalin, β-casomorphin, and leucokinin, were analyzed by a multiplexed MS/MS approach of the sort described herein. FIG. 9A displays the mass spectrum of these 5 peptide accumulated at a LMCO of 48 Da (rf voltage=301 $V_{p-p}$), and FIG. 9B shows the mass spectrum of these 5 singly-charged peptide ions after isolatation using the stored-waveform inverse Fourier transform (SWIFT) method. The [M+H]+ ions of these peptides appear at m/z 421, 482, 556, 659, and 783 for TRH-Gly, angiotensinogen, leucine enkephalin, β-casomorphin, and leucokinin, respectively. Simultaneous dissociation of these 5 peptide ions using a second SWIFT waveform results in a first product ion spectrum shown in FIG. 10.

Example 3b

Figure 11:
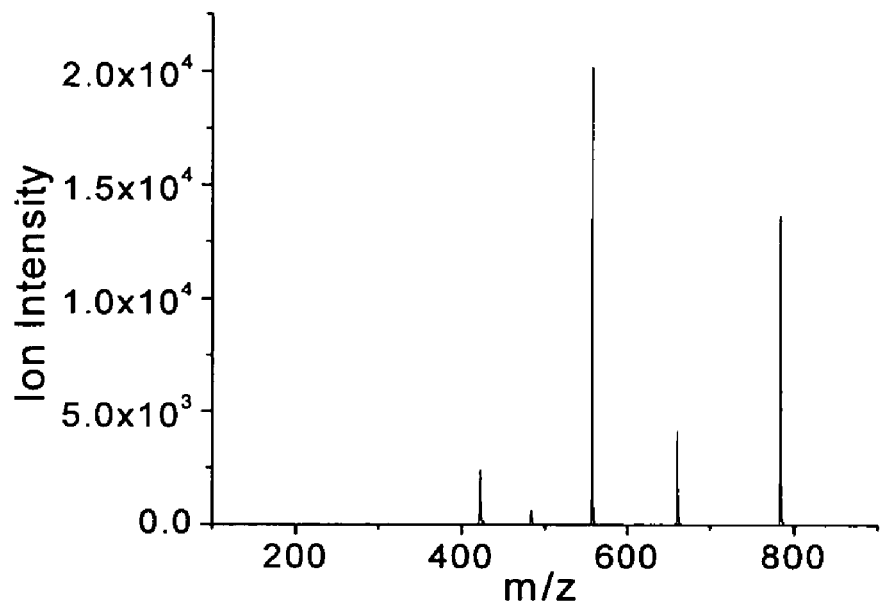
FIG. 11: Mass spectrum of a mixture of 5 peptides (TRH-Gly, angiotensinogen, leucine enkephalin, β-casomorphin, and leucokinin) after SWIFT isolation at a LMCO value of 58 Da.

The same 5 peptide ions are then accumulated at a different LMCO value, with their intensities changed as described above. FIG. 11 shows the mass spectrum of the 5 SWIFT isolated peptide after ion accumulation at a LMCO of 58 Da (rf voltage=364 $V_{p-p}$). Comparing the spectrum with FIG. 9B, it is evident that the parent ion intensities have changed. The expected parent ion intensity changes can be calculated using equation 1, and Table 1 provides a comparison of the experimentally observed and predicted intensity changes after accumulating the ions at this new LMCO value. Table 1 shows that with the exception of the peptide TRH-Gly the observed and calculated intensity changes are very close. (A discussion about the deviation for TRH-Gly is provided in example 3e, below). Simultaneous SWIFT dissociation of these 5 peptide ions, accumulated at the new LMCO value, results in a second product ion spectrum shown in FIG. 12. In actual practice, the spectrum shown in FIG. 11 would not need to be acquired because the intensity changes are predictable, according to the relationship of Equation 1. (In other words, FIG. 11 illustrates the point that the parent ion intensities change in a predictable manner.)

TABLE 1

Experimentally Observed and Calculated Intensity Changes for the 5 Peptide Ions.

| Peptide Ion | Observed Intensity Ratio (1°/2°)[a] | Calculated Intensity Ratio (1°/2°)[b] |
|---|---|---|
| Leucokinin (m/z 783) | 1.2 | 1.2 |
| β-casomorphin (m/z 659) | 2.1 | 1.9 |
| Leucine enkephalin (m/z 556) | 2.4 | 2.7 |
| Angiotensinogen (m/z 482) | 3.2 | 3.7 |
| TRH-Gly (m/z 421) | 1.9 | 4.5 |

[a]Determined by dividing the ion intensity from the spectrum in FIG. 9B by the ion intensity in FIG. 11.
[b]Determined using the LMCO variation of equation 1

Example 3c

Figure 10:
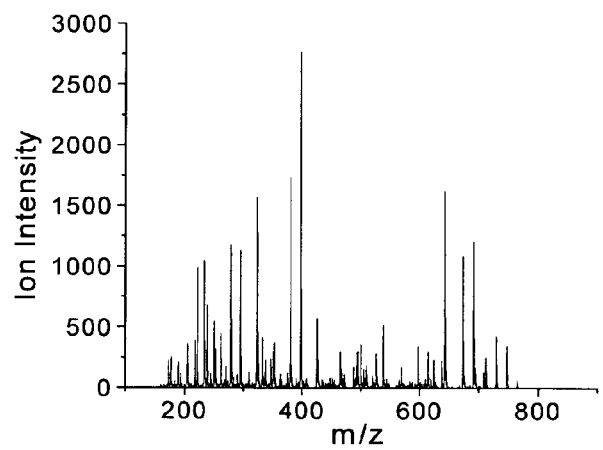
FIG. 10: Product ion spectrum (MS/MS) after simultaneous dissociation of 5 peptide ions from FIG. 9B (LMCO accumulation value=48 Da).
Figure 12:
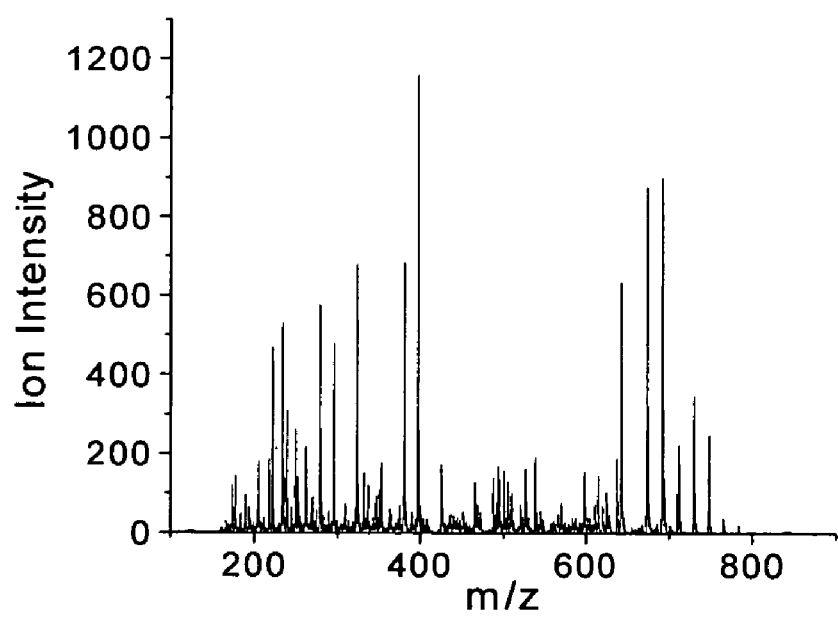
FIG. 12: Product ion spectrum (MS/MS) after simultaneous dissociation of 5 peptide ions from FIG. 11 (LMCO accumulation value=58 Da).
Figure 13:
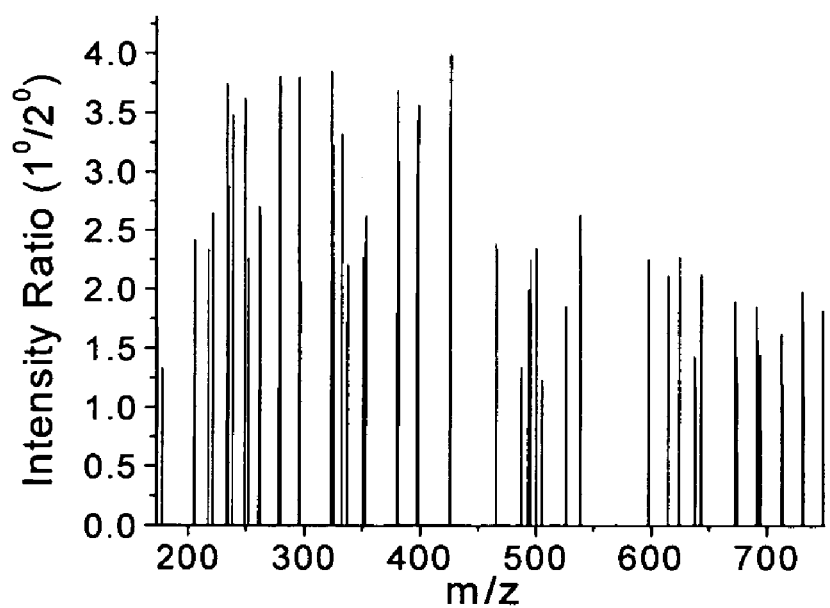
FIG. 13: Ratio spectrum obtained by dividing the primary spectrum (FIG. 10) by the secondary spectrum (FIG. 12).
Figure 14:
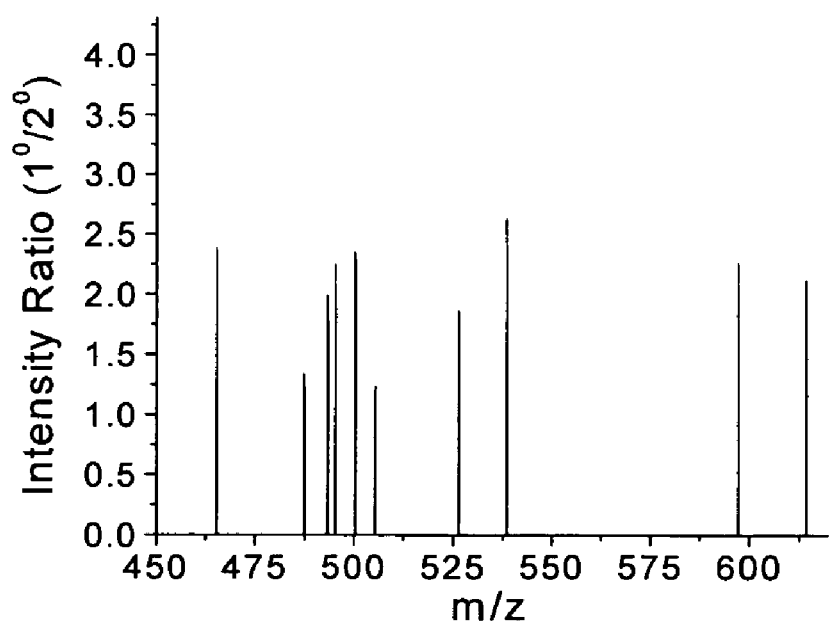
FIG. 14: Expanded region between m/z 450 and 625 of the Ratio Spectrum in FIG. 13.

A comparison of the first product ion spectrum shown in FIG. 10 with a second product ion spectrum in FIG. 12 indicates that the intensities of many of the product ions have changed, although a simple visual inspection of these two spectra may not, in all instances, clearly indicate the intensity changes. A more convenient means of determining the intensity changes and thus identifying the parent ion from which each product ion arises is to use a ratio spectrum. If the primary (product ion) spectrum in FIG. 10 is divided by the secondary (product ion) spectrum in FIG. 12, a ratio spectrum is obtained (FIG. 13). FIG. 13 was obtained by first subtracting out any ions with intensities below 150, which removes any noise that would ultimately be amplified in the ratio spectrum while assuming no useful information is deleted. From the ratio spectrum in FIG. 13, linking the parent and product ions can be accomplished by identifying the product ion m/z values that appear at the ratios shown in Table 1. For instance, FIG. 14 shows an expanded region of FIG. 13 from m/z 450 to 625. In this region 13 different product ions are present. The m/z and intensity ratios of these product ions are listed in Table 2 along with their parent ions, which were determined by comparing the product ions' intensity ratios with the expected parent ion ratios shown in Table 1. With the exception of m/z 493 and 526, the intensity encoding scheme allowed all the product ions in this range to be correctly associated with their appropriate parent ion. The product ions at m/z 493 and 526 both have intensity ratios of about 1.8, while their parent ions, leucine enkephalin and leucokinin, were encoded at 2.4 and 1.2, respectively. Close inspection of FIGS. 10 and 12 indicate that m/z 493 has intensities of 274 and 150, respectively, while m/z 526 has intensities of 288 and 155, respectively. The later intensities, each in the corresponding secondary spectrum, are both very close to the value of 150 chosen for noise removal, showing the foregoing assumption can be adjusted as needed.

TABLE 2

Product Ions Between m/z 450 and 625 in the Ratio Spectrum (FIG. 14) and Their m/z Ratios, Intensity Ratios, and Identified Parent Ions.

| Product Ion (m/z) | Product Ion Intensity Ratio (1°/2°) | Identified Parent Ion (Parent Ion Intensity Ratio)[a] |
|---|---|---|
| 465 | 2.4 | Leucine enkephalin (2.4) |
| 487 | 1.3 | Leucokinin (1.2) |
| 493 | 2.0 | — |
| 495 | 2.2 | β-casomorphin (2.1) |
| 500 | 2.2 | β-casomorphin (2.1) |
| 505 | 1.2 | Leucokinin (1.2) |
| 526 | 1.8 | — |
| 538 | 2.6 | Leucine enkephalin (2.4) |
| 597 | 2.2 | β-casomorphin (2.1) |
| 614 | 2.1 | β-casomorphin (2.1) |

[a]Parent ion intensity ratio from Table 1

Example 3d

Figure 15:
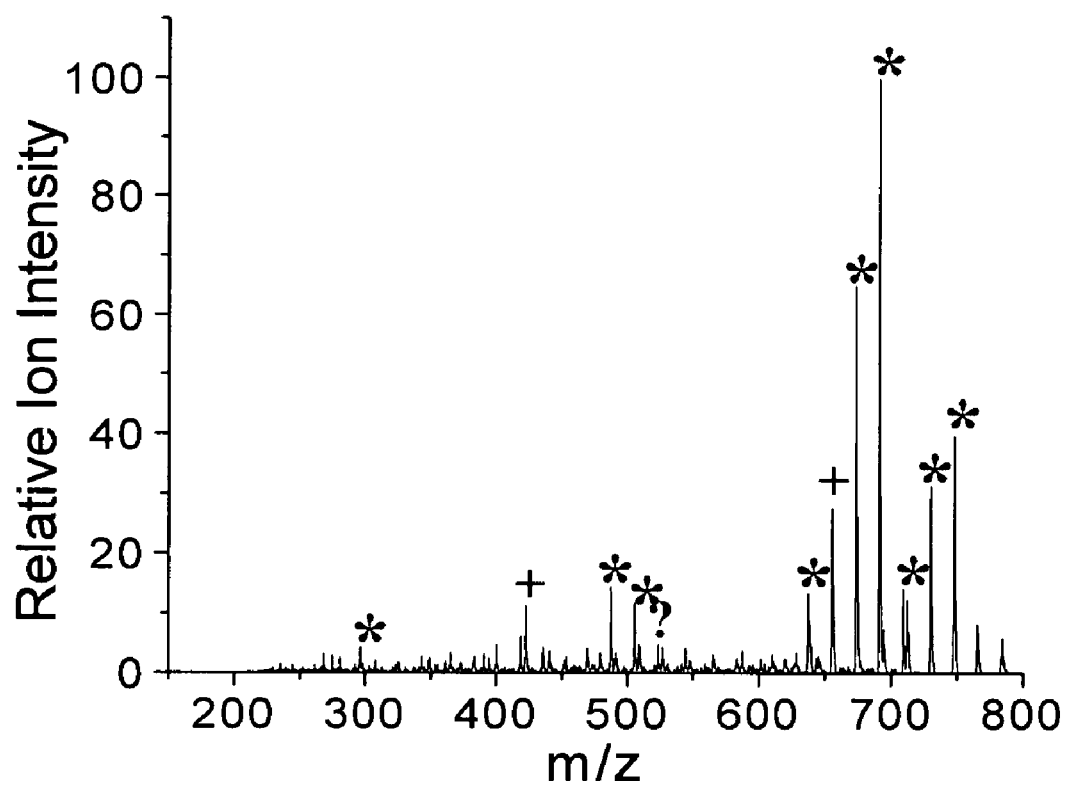
FIG. 15: Product ion spectrum (MS/MS) of an authentic sample of leucokinin, which demonstrates the number of its product ions identified by the multiplexed MS/MS approach. The peaks with an asterisk (*) above them are the product ions that were correctly identified during the multiplexed MS/MS experiment. The peaks with the plus sign (+) above them are product ions that were not identified during the multiplexed MS/MS experiment because these ions have m/z values close to those of other parent ions and thus their detection is precluded by the SWIFT waveforms used to dissociate these parent ions. The peak with a question mark (?) above it corresponds to a product ion that was present in the ratio spectrum, but its intensity ratio was deemed to be too far from the expected intensity ratio for leucokinin (i.e. 1.2).

Another means by which this data can be displayed is to show the authentic MS/MS spectrum of one of the parent ions with an indication of the product ions identified during the multiplexed MS/MS analysis. FIG. 15 shows the product ion spectrum for leucokinin. The peaks with an asterisk (*) above them are the product ions that were correctly identified during the multiplexed MS/MS experiment. The peaks with the plus sign (+) above them are product ions that were not identified during the multiplexed MS/MS experiment because these ions have m/z values close to those of other parent ions and thus their detection is precluded by the SWIFT waveforms used to dissociate these parent ions. Product ions at m/z 422, which is close to the m/z of TRH-Gly (m/z 421), and m/z 655, which is close to the m/z of β-casomorphin (m/z 659) are the two ions that fall into this category. The peak with a question mark (?) above it corresponds to a product ion that was present in the ratio spectrum, but its intensity ratio was deemed to be too far from the expected intensity ratio for leucokinin (i.e. 1.2). This ion at m/z 526 was found to have an intensity ratio of 1.8. Again, as noted above, a miscoding of this ion is likely due to its low intensity, which is close to the noise level. The other peaks in FIG. 15, which were not identified, likely were removed when the "noise" was subtracted to obtain the ratio spectrum in FIG. 13. As noted above some useful information is lost by removing the noise.

Example 3e

Figure 16:
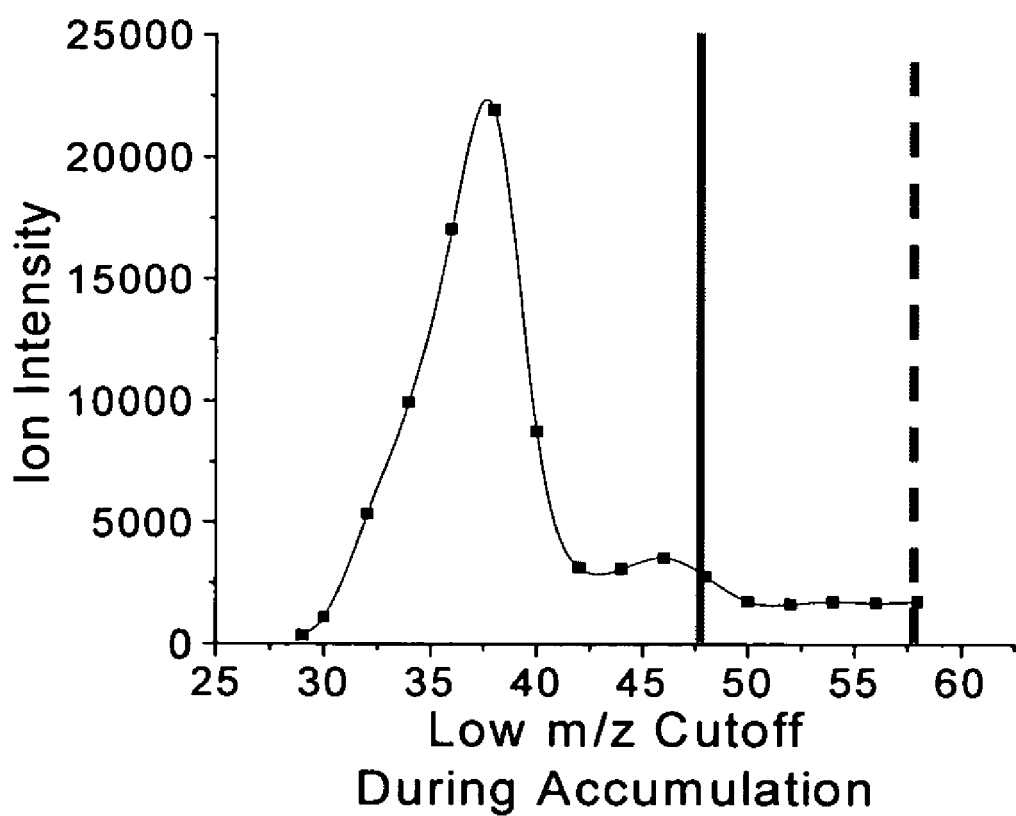
FIG. 16: Ion intensity distribution for TRH-Gly (m/z 421) as a function of LMCO during ion accumulation. The solid line shows the LMCO accumulation value used during acquisition of the spectrum in FIG. 9B, and the dotted line shows the LMCO value used during acquisition of the spectrum in FIG. 11.

As observed in Table 1, the peptide TRH-Gly (m/z 421) was not optimally encoded. The observed encoding of m/z 421 can be understood by observing FIG. 16. The ion intensity vs. LMCO plot for this ion shows some "tailing" of the Gaussian distribution at higher LMCO values. This tailing occurs to some degree for all peptide ions, but it only has a detrimental effect on predicting the intensity change if the LMCO values used to acquire both the primary and secondary spectra occur in this "tailing" region. The lines in FIG. 16 show the LMCO values at which the primary and secondary spectra were acquired for FIGS. 9 through 12. A first assumption useful in conjunction with this methodology is that the distribution of ion intensities as a function of LMCO is Gaussian. However, the distribution may indeed be a modified Gaussian distribution. The effects of ion injection parameters on this distribution may, for a particular ion, suggest an adjustment of primary and secondary rf voltages to avoid spectra acquisition in such a tailing region.

Example 4

To promote a better fundamental understanding of why a Gaussian relationship exists between ion abundance and the LMCO used during ion accumulation, effort has been made to understand how to control/change these Gaussian distributions for better performance. From this work, it was identified that the distribution of ion kinetic energies as ions enter the quadrupole ion trap is a factor easily controllable from an experimental standpoint if one desires to control/change the observed Gaussian distributions.

An experimental variable on the particular quadrupole ion trap mass spectrometer used was found to easily vary the distribution of ion kinetic energies. For any quadrupole ion trap mass spectrometer in which ions are generated externally, a series of electrodes with applied voltages are used to direct ions into the mass analyzer. These electrodes and the associated voltages applied to them ultimately control the distribution of ion kinetic energies. On the Bruker Esquire-LC quadrupole ion trap mass spectrometer described above, it was observed that variation of the dc offset on octopole 1 provides good experimental control of the ion kinetic energy distribution. By varying the dc potential applied to this lens element, ion abundance as a function of the LMCO can be significantly changed (see FIG. 17).

Figure 17:
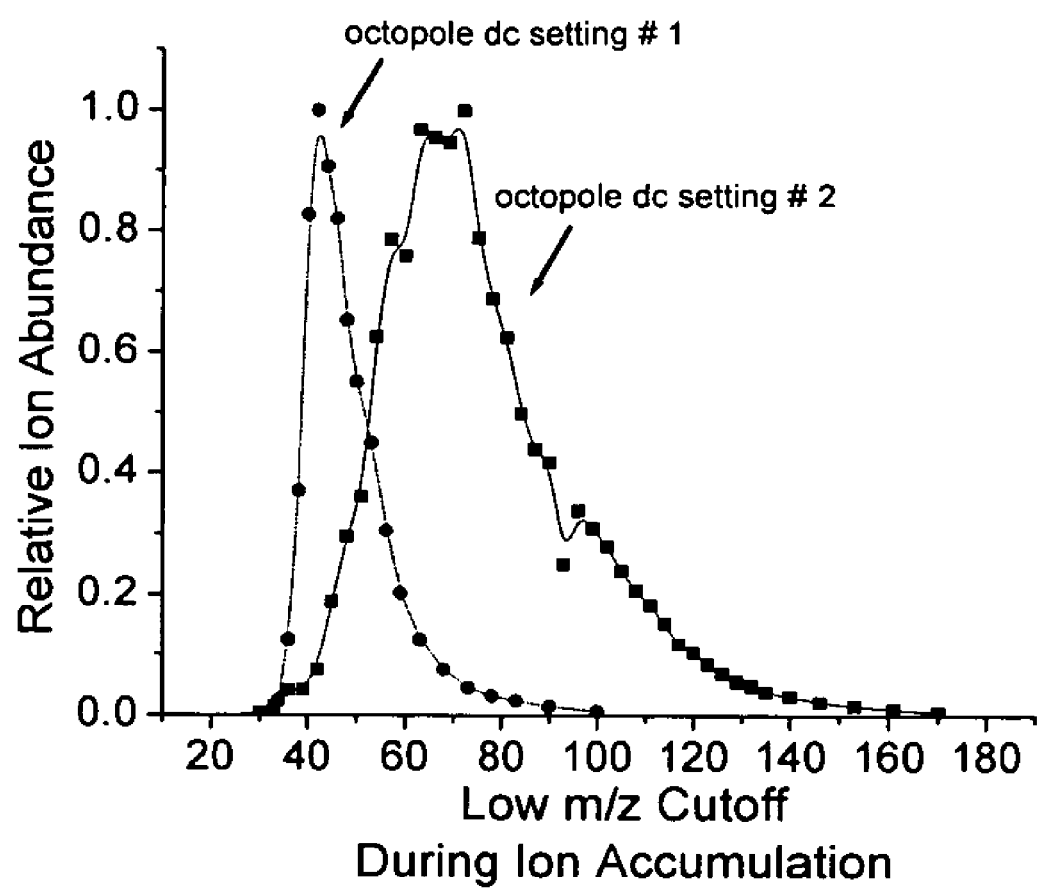
FIG. 17: Normalized ion abundance distribution for the protonated peptide ion (M+H)$^+$ of leucine enkephalin as a function of LMCO during ion accumulation for two different octopole dc settings.

While the practical implications of this observation with regards to this invention are not entirely clear at this point, because the present methods relate to distributions like those shown in FIG. 17, understanding how to control these distributions can be used to increase the overall flexibility of this spectrometric approach.

As shown above, multiplexed MS/MS can be used for a collection of n (e.g., in this example 3, n=5) peptide ions in which only two product ion spectra are necessary to obtain the appropriate relationships between parent and product ions. This is an advantage over serial MS/MS in which five product ion spectra would be required to obtain the same information. The multiplexed MS/MS approach of this invention encodes the parent ions according to their intensity. This intensity encoding can be accomplished by recognizing that in a quadrupole ion trap mass spectrometer the intensity of a given parent ion displays a Gaussian distribution with respect to the rf voltage applied to the ring electrode during ion accumulation. The centers of these Gaussian distributions increase in a linear fashion as the m/z ratios of the parent ions increase. Furthermore, the widths (at 50%) of these distributions are relatively constant and independent of m/z. By changing the rf accumulation voltage from one spectrum to the next, parent ions (and thus their resulting product ions) can be encoded in a predictable manner. The appropriate parent/product ion relationships can then be determined by comparing the intensity changes of the product ions with the expected intensity changes of the parent ions.

We claim:

1. An ion trap mass spectrometric method for resolving a mixture of compounds, said method comprising:
   providing first spectra comprising a spectrum of a plurality of compound parent ions, and a spectrum of at least one product ion of each said parent ion, said first spectra acquired under a first set of ion trapping conditions;
   providing second spectra comprising a spectrum of a plurality of compound parent ions, and a spectrum of at least one product ion of each said parent ion, said second spectra acquired under a second set of ion trapping conditions;
   determining the fractional change in each parent ion accumulated over said first and second spectra; and
   applying said parent ion fractional change to at least one of said product ions in said first and second product ion spectra, to determine a product for each said parent ion.

2. The method of claim 1 wherein said ion trapping conditions are selected from at least one of rf voltage applied to a ring electrode during said accumulation, and a predetermined low m/z cut off.

3. The method of claim 2 wherein said spectra are acquired over different applied rf voltages, and said fractional change, $F_{1-2}$, is expressed by $$F_{1-2} = \frac{e^{\left(\frac{-(rf2-c)^2}{2w^2}\right)}}{e^{\left(\frac{-(rf1-c)^2}{2w^2}\right)}}$$

wherein e is the natural log base, rf1 is a first applied voltage and rf2 is a second applied voltage, c is the center of a Gaussian distribution of said parent ion accumulation, and w is the width at one-half the height of said Gaussian distribution.

4. The method of claim 1 wherein said parent ion accumulation is measured by one of ion abundance and ion intensity.

5. The method of claim 1 comprising provision of third spectra comprising a spectrum of a plurality of compound parent ions, and a spectrum of at least one product ion of each said parent ion, said third spectra acquired under a third set of ion trapping conditions.

6. The method of claim 1 comprising a liquid chromatographic separation selected from prior to said product ion determination and after said product ion determination.

7. A method of using quadrupole ion trap mass spectrometry for multiplexed determination of multiple parent/product ion relationships, said method comprising:
   providing a quadrupole ion trapping mass spectrometer;
   providing at least two mass spectra, each said spectrum comprising product ions of a plurality of parent ions, each said spectrum generated at a different rf voltage;
   calculating a fractional change in ion abundance for each said parent ion; and
   determining product ions having a change in abundance, over each said spectrum, corresponding to said calculated fractional change for each said parent ion.

8. The method of claim 7 wherein said fractional change, $F_{1-2}$, is expressed by $$F_{1-2} = \frac{e^{\left(\frac{-(rf2-c)^2}{2w^2}\right)}}{e^{\left(\frac{-(rf1-c)^2}{2w^2}\right)}}$$

wherein e is the natural log base, rf1 is a first applied voltage and rf2 is a second applied voltage, c is the center of a Gaussian distribution of said parent ion accumulation, and w is the width at one-half the height of said Gaussian distribution.

9. The method of claim 7 comprising generation of two mass spectra.

10. The method of claim 9 wherein said determination comprising acquisition of a ratio spectrum comparing the quotient of said spectra with said fractional change in parent ion abundance.

11. A method of using quadrupole ion trapping mass spectrometry for multiplexed determination of a peptide mixture, said method comprising:
providing a quadrupole ion trapping mass spectrometer;
providing at least two mass spectra, each spectrum comprising product ions of a plurality of peptide parent ions, each said spectrum generated under different ion trapping conditions, said conditions selected from one of rf voltage and a predetermined low m/z cut off;
calculating a fractional change in ion accumulation for each said peptide parent ion; and
determining product ions having an accumulation change, over said spectra, corresponding to said calculated fractional change for each said peptide parent ion.

12. The method of claim 11 wherein said fractional change, $F_{1°-2°}$, is expressed by $$F_{1°-2°} = \frac{e^{\left(\frac{-[LMCO(1°)-c]^2}{2w^2}\right)}}{e^{\left(\frac{-[LMCO(2°)-c]^2}{2w^2}\right)}}$$

wherein e is the natural log base, LMCO(1°) is a first low m/z cut off and LMCO(2°) is a second low m/z cut off, c is the center of a Gaussian distribution, and w is the width at one-half the height of said Gaussian distribution.

13. The method of claim 12 wherein said peptide parent ion accumulation is measured by one of ion abundance and ion intensity.

14. The method of claim 12 wherein said peptide parent ion accumulation is measured by ion intensity.

15. The method of claim 14 comprising generation of two spectra.

16. The method of claim 15 wherein said determination comprises acquisition of a ratio spectrum comparing the quotient of said spectra with said fractional change in peptide parent ion intensity.

17. The method of claim 11 used with a proteomic assessment.

18. A method of using Gaussian distribution to assess product ion mass spectra, from a quadrupole ion trap mass spectrometer said method comprising:
providing an m/z parent ion accumulation exhibiting a Gaussian distribution as a function of voltages applied to the quadrupole ion trap, with said distribution providing a center value, c, and a width value, w, for each said accumulation;
determining a fractional change in parent ion accumulation; and
applying said fractional change to a first product ion spectrum to assess a second product ion spectrum, to associate said product ion spectra with each said parent ion.

19. The method of claim 18 wherein said parent ion accumulation is measured by one of ion abundance and ion intensity.

20. The method of claim 18 wherein said voltages are applied to a ring electrode during said accumulation.

* * * * *